United States Patent
Guillonneau et al.

(10) Patent No.: US 10,591,465 B2
(45) Date of Patent: Mar. 17, 2020

(54) METHODS AND KITS FOR LABELING, DETECTION AND ISOLATION OF FOXP3+ REGULATORY T CELLS, ISOLATED POPULATION OF FOXP3+ REGULATORY T CELLS THUS OBTAINED AND USES THEREOF

(71) Applicants: INSERM (INSTITUT NATIONAL DE LA SANTE ET DE LA RECHERCHE MEDICALE), Paris (FR); UNIVERSITE DE NANTES, Nantes (FR); CENTRE HOSPITALIER UNIVERSITAIRE DE NANTES, Nantes (FR)

(72) Inventors: Carole Guillonneau, Nantes (FR); Ignacio Anegon, Nantes (FR); Severine Bezie, Nantes (FR)

(73) Assignees: INSERM (INSTITUT NATIONAL DE LA SANTÉ ET DE LA RECHERCHE MÉDICALE), Paris (FR); UNIVERSITÉ DE NANTES, Nantes (FR); CENTRE HOSPITALIER UNIVERSITAIRE DE NANTES, Nantes (FR)

( * ) Notice: Subject to any disclaimer, the term of this patent is extended or adjusted under 35 U.S.C. 154(b) by 0 days.

(21) Appl. No.: 15/573,068

(22) PCT Filed: May 12, 2016

(86) PCT No.: PCT/EP2016/060778
§ 371 (c)(1),
(2) Date: Nov. 9, 2017

(87) PCT Pub. No.: WO2016/180948
PCT Pub. Date: Nov. 17, 2016

(65) Prior Publication Data
US 2018/0106779 A1    Apr. 19, 2018

(30) Foreign Application Priority Data

May 12, 2015    (EP) ..................................... 15305715

(51) Int. Cl.
| | | |
|---|---|---|
| G01N 33/50 | (2006.01) | |
| G01N 33/569 | (2006.01) | |
| G01N 33/68 | (2006.01) | |
| C12N 5/0783 | (2010.01) | |
| A61K 35/17 | (2015.01) | |
| A61K 35/12 | (2015.01) | |

(52) U.S. Cl.
CPC ........... *G01N 33/505* (2013.01); *A61K 35/17* (2013.01); *C12N 5/0637* (2013.01); *G01N 33/56972* (2013.01); *G01N 33/6869* (2013.01); *A61K 2035/122* (2013.01); *C12N 2501/2334* (2013.01); *G01N 2333/7051* (2013.01); *G01N 2333/70514* (2013.01); *G01N 2333/70517* (2013.01); *G01N 2333/70589* (2013.01); *G01N 2800/245* (2013.01)

(58) Field of Classification Search
None
See application file for complete search history.

(56) References Cited

U.S. PATENT DOCUMENTS

| | | |
|---|---|---|
| 4,230,685 A | 10/1980 | Senyei et al. |
| 4,452,773 A | 6/1984 | Molday |
| 4,486,414 A | 12/1984 | Pettit |
| 4,770,183 A | 9/1988 | Groman et al. |
| 4,816,444 A | 3/1989 | Pettit et al. |
| 4,879,278 A | 11/1989 | Pettit et al. |
| 4,978,744 A | 12/1990 | Pettit et al. |
| 4,986,988 A | 1/1991 | Pettit et al. |
| 5,076,973 A | 12/1991 | Pettit et al. |
| 5,138,036 A | 8/1992 | Pettit et al. |
| 5,410,024 A | 4/1995 | Pettit et al. |
| 5,504,191 A | 4/1996 | Pettit et al. |

(Continued)

FOREIGN PATENT DOCUMENTS

| | | |
|---|---|---|
| EP | 2597463 A1 | 5/2013 |
| WO | 9409117 A1 | 4/1994 |

(Continued)

OTHER PUBLICATIONS

Duhen et al., Blood. May 10, 2012; 119(19): 4430-4440 (Year: 2012).*
Saar Gill, et al., Going viral: chimeric antigen receptor T-cell therapy for hematological malignancies, Immunological Reviews, 2015, pp. 68-89, vol. 263, John Wiley & Sons Ltd.

(Continued)

*Primary Examiner* — Daniel C Gamett
(74) *Attorney, Agent, or Firm* — Young & Thompson

(57) ABSTRACT

Disclosed is a method for labeling, detecting and/or isolating Foxp3+ Treg cells from a biological sample containing peripheral blood mononuclear cells (PBMC) or lymphocytes including the following steps of: (i) coupling the surface of PBMC or lymphocytes to a capture moiety which binds to the cell through a cell surface molecule and to interleukin-34 (IL34), (ii) culturing the lymphocytes under conditions wherein IL34 is secreted, released and specifically captured by the capture moiety, (iii) labeling the IL34 expressing lymphocytes with a label moiety, and (iv) optionally detecting and/or isolating the IL34 expressing lymphocytes which are Foxp3+ Treg cells. Also disclosed is an isolated population of Foxp3+ Treg cells obtainable by the method and uses thereof.

17 Claims, 3 Drawing Sheets

(56) References Cited

U.S. PATENT DOCUMENTS

Figure 1A:
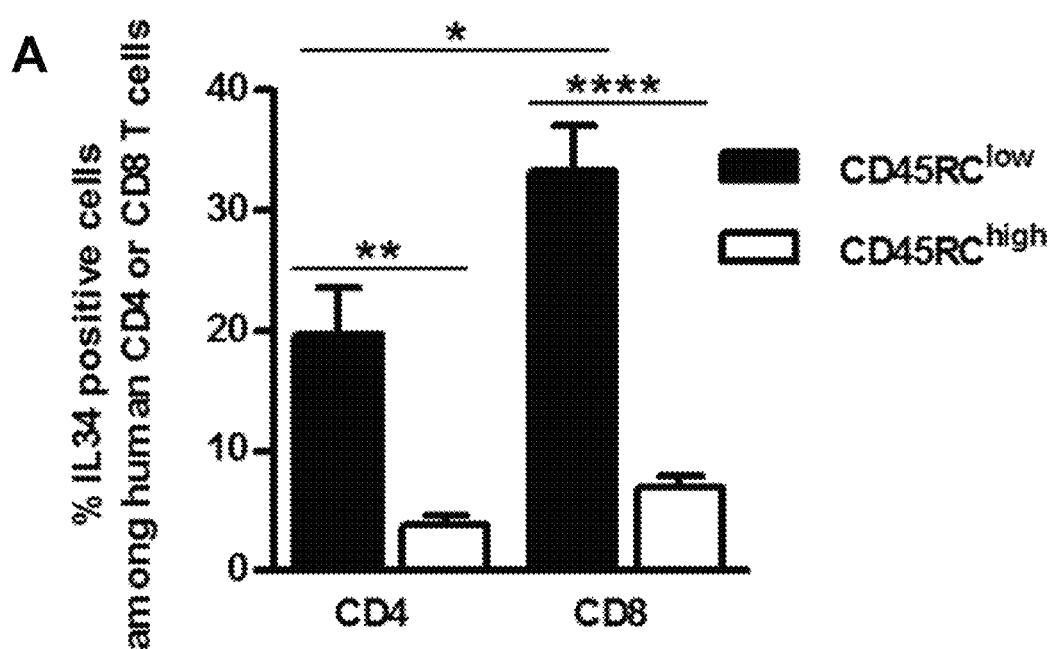

| | | | |
|---|---|---|---|
| 5,521,284 | A | 5/1996 | Pettit et al. |
| 5,530,097 | A | 6/1996 | Pettit et al. |
| 5,554,725 | A | 9/1996 | Pettit |
| 5,599,902 | A | 2/1997 | Pettit et al. |
| 5,635,483 | A | 6/1997 | Pettit et al. |
| 5,663,149 | A | 9/1997 | Pettit et al. |
| 5,665,860 | A | 9/1997 | Pettit et al. |
| 5,780,588 | A | 7/1998 | Pettit et al. |
| 6,034,065 | A | 3/2000 | Pettit et al. |
| 6,239,104 | B1 | 5/2001 | Pettit et al. |
| 6,323,315 | B1 | 11/2001 | Pettit et al. |
| 6,884,869 | B2 | 4/2005 | Senter et al. |
| 2003/0083263 | A1 | 5/2003 | Doronina et al. |

FOREIGN PATENT DOCUMENTS

| | | |
|---|---|---|
| WO | 02/088172 | 11/2002 |
| WO | 04/010957 | 2/2004 |
| WO | 2010101870 A1 | 9/2010 |
| WO | 2013119716 A1 | 8/2013 |
| WO | 2016009041 A1 | 1/2016 |

OTHER PUBLICATIONS

Michael Jensen, et al., Designing Chimeric Antigen Receptors to Effectively and Safely Target Tumors, Current Opinion in Immunology, Apr. 2015, pp. 9-15, vol. 33, Elsevier Ltd.

Joanna Wieckiewicz, et al., T regulatory cells and the control of alloimmunity: from characterisation to clinical application, Current Opinion in Immunology, 2010, pp. 662-668, vol. 22, Elsevier Ltd.

Shivani Srivastava, et al., Engineering CAR-T Cells: Design Concepts, Trends in Immunology, Aug. 2015, pp. 494-502, vol. 36, No. 8.

Chiara Bonini, et al., Adoptive T-cell therapy for cancer: The era of engineered T cells, European Journal of Immunology, 2015, pp. 2457-2469, vol. 45, Wiley-VCH Verlag GmbH & Co. KGaA.

Olivia Weigert, et al., CD4+ Foxp3+ regulatory T cells prolong drug-induced disease remission in (NZBxNZW) F1 lupus mice, Arthritis Research & Therapy, pp. 1-11, vol. 15, R35.

Sharvan Sehrawat, et al., In Vitro-Generated Antigen-Specific CD4+ CD25+ Foxp3+ Regulatory T Cells Control the Severity of Herpes Simplex Virus-Induced Ocular Immunoinflammatory Lesions, Jul. 2008, pp. 6838-6851, vol. 82, No. 14.

Herman Waldmann, et al., Harnessing FOXP3+ regulatory T cells for transplantation tolerance, The Journal of Clinical Investigation, Apr. 2014, pp. 1439-1445, vol. 124, No. 4.

Renee Robb, et al., Identification and expansion of highly suppressive CD8+FoxP3+ regulatory T cells after experimental allogeneic bone marrow transplantation, Blood Journal, Jun. 14, 2012, pp. 5898-5908, vol. 119, No. 24.

Laurence Ordonez, et al., CD45RC Isoform Expression Identifies Functionally Distinct T Cell Subsets Differentially Distributed between Healthy Individuals and AAV Patients, PLoS One, Apr. 2009, pp. 1-10, vol. 4, Issue 4.

Laurence Ordonez, et al., A Higher Risk of Acute Rejection of Human Kidney Allografts Can Be Predicted from the Level of CD45RC Expressed by Recipients' CD8 T Cells, PLoS One, Jul. 2013, pp. 1-12, vol. 8, Issue 7.

Suwen Wei, et al., Functional overlap but differential expression of CSF-1 and IL-34 in their CSF-1 receptor-mediated regulation of myeloid cells, Journal of Leukocyte Biology, Sep. 2010, pp. 495-505, vol. 88.

International search report for Application No. PCT/EP2016/060778, dated Jun. 16, 2016.

* cited by examiner

METHODS AND KITS FOR LABELING, DETECTION AND ISOLATION OF FOXP3+ REGULATORY T CELLS, ISOLATED POPULATION OF FOXP3+ REGULATORY T CELLS THUS OBTAINED AND USES THEREOF

FIELD OF THE INVENTION

The invention relates to methods for labeling, detecting and isolating forkhead box P3 (Foxp3+) regulatory T cells (also referred to as Foxp3+ Treg cells) from a biological sample, kits for labeling, detecting and isolating Foxp3+ Treg cells, as well as the isolated population of Foxp3+ Treg cells thus obtained and the uses thereof including therapeutic uses in the fields of autoimmunity, allergy, transplantation. The invention also relates to prognostic methods based on detection of said Foxp3+ Treg cells in a biological sample obtained from a patient.

BACKGROUND OF THE INVENTION

Foxp3+ regulatory T cells, or "Tregs" are fundamental in controlling various immune responses in that Tregs can rapidly suppress the activity of other immune cells. In particular, Tregs are crucial for maintaining tolerance by downregulating undesired immune responses to self and non-self antigens. For instance, Treg defects have been discovered in patients with multiple sclerosis (MS), type I diabetes (T1D), psoriasis, myasthenia gravis (MG) and other autoimmune diseases. Similar links may also exist for atopy and allergic diseases. For all these diseases reports exist pointing to a reduced in vitro immune suppression of the patient's Treg cells. This has led to an increasing interest in the possibility of using Tregs in immunotherapy to treat or prevent, autoimmune diseases, allergies and transplantation-related complications, such as graft rejection or graft-versus-host disease (GvHD) (1).

Methods for the isolation of human CD4+ Foxp3+ Treg cells are known. All of the hitherto described methods for isolation of human Foxp3+ Treg cells employ positive selection of Foxp3+ Treg cells based on cell surface markers of Tregs. That is, the Foxp3+ Treg cells are isolated by using antibodies for Treg associated cell surface markers, mostly CD25+ and CD127−. Yet most cell surface markers of Tregs, such as CD4 and CD25, are not restricted to Tregs. For instance, the commonly employed CD25 is not present on all Foxp3+ Treg cells and is also expressed by effector and memory CD4+ T cells. Consequently, disadvantage of current methods is the contamination of the isolated Treg subsets with effector T cells. When employing markers such as CD25 these contaminations can be significant as up to half of the isolated CD4+ cell population can be comprised of effector T cells. Moreover, it should be further highlighted that there is no method known to isolate CD8+ Foxp3+ Tregs since research has focused on the CD4+ Foxp3+ Tregs. Thus, specific cell surface marker has not yet been identified. However, CD8+ Foxp3+ Tregs also represents an efficient approach for maintaining or inducing tolerance (2).

Hence, there is a particular need for methods and kits/compositions useful for isolating Foxp3+ Treg cells with high degree of purity, and simultaneously CD4+ and CD8+ Foxp3+ Tregs, which are virtually free from CD4+ and CD8+ effector T cells in order to obtain an isolated and purified population of Foxp3+ Treg cells which may be then expanded and pulsed with antigens of interest in order to efficiently induce antigen-specific immune tolerance. Such primed population of Foxp3+ Treg cells is particularly of interest in the fields of autoimmunity, allergy, transplantation, treatment with therapeutic protein and gene therapy, to avoid degradation of self or therapeutic molecules/tissues by the immune system and in cancer to determine the prognosis of a subject suffering from a cancer.

SUMMARY OF THE INVENTION

In a first aspect, the invention relates to a method for labeling, detecting and/or isolating forkhead box P3 (Foxp3+) regulatory T cells (Foxp3+ Treg cells) from a biological sample containing peripheral blood mononuclear cells (PBMC) or lymphocytes comprising the following steps of: (i) coupling the surface of PBMC or lymphocytes to a capture moiety which binds to the cell through a cell surface molecule and to Interleukin-34 (IL34), (ii) culturing the lymphocytes under conditions wherein IL34 is secreted, released and specifically captured by the capture moiety, (iii) labeling the IL34 expressing lymphocytes with a label moiety, and (iv) optionally detecting and/or isolating said IL34 expressing lymphocytes which are Foxp3+ Treg cells.

In a second aspect, the invention relates to an in vitro method for determining whether a patient is at risk of transplant rejection, autoimmune diseases, unwanted immune response against therapeutic proteins or allergies, comprising a step of determining the presence Foxp3+ Treg cells in a biological sample obtained from said patient by a method of the invention, wherein the presence of Foxp3+ Treg cells is indicative of a reduced risk of transplant rejection, autoimmune diseases, unwanted immune response against therapeutic proteins or allergies.

In a third aspect, the invention relates to a kit comprising at least one capture moiety which binds to the cell through a cell surface molecule and to IL34 and a labeled moitey.

In a fourth aspect, the invention relates to an bispecific antibody selected from the group consisting of a bispecific antibody which binds to CD3 and IL34, a bispecific antibody which binds to CD4 and IL34, a bispecific antibody which binds to CD8 and IL34, a bispecific antibody which binds to CD45 and IL34, a bispecific antibody which binds to the TCR and IL34, and a bispecific antibody which binds to the chimeric antigen receptor and IL34.

In a fifth aspect, the invention relates to an isolated population of Foxp3+ Treg cells obtainable by a method of the invention.

In a sixth aspect, the invention relates to a method for obtaining a population of antigen-specific Foxp3+ Treg cells comprising the steps of: (i) culturing the population of Foxp3+ Treg cells with a culture medium comprising an amount of antigen; and (ii) isolating the population of antigen-specific Foxp3+ Treg cells.

In a seventh aspect, the invention relates to isolated population of antigen-specific Foxp3+ Treg cells obtainable by a method of the invention.

DETAILED DESCRIPTION OF THE INVENTION

The invention is based on results about the interleukin-34 (IL34) expression, more particularly secretion, by Foxp3+ Treg cells (especially Foxp3+ CD4+ and CD8+ Tregs).

The inventors have indeed shown that IL34 expression on T cells was specific of CD4+Foxp3+ and CD8+Foxp3+ Tregs versus CD4+Foxp3− and CD8+Foxp3− T cells subsets, indicating that IL34 is a Foxp3+ Treg-specific cytokine that may play a crucial role in Treg-mediated tolerance. Accordingly, isolation of Foxp3$^+$ Treg cells using the method according to the invention as defined below is faster, easier and above all more effective with regard to the isolation of a uniform population that accounts for most of the Foxp3$^+$ Treg cells contained in a biological sample. In other words, isolation of Foxp3$^+$ Treg cells employing the method of the invention yields a population of immune-suppressive Foxp3$^+$ Treg cells that is virtually free from contaminating CD4$^+$ and CD8$^+$ effector T cells.

In a first aspect, the invention thus relates to a method for labeling, detecting and/or isolating forkhead box P3 (Foxp3$^+$) regulatory T cells (Foxp3$^+$ Treg cells) from a biological sample containing peripheral blood mononuclear cells (PBMC) or lymphocytes comprising the following steps of: (i) coupling the surface of PBMC or lymphocytes to a capture moiety which binds to the cell through a cell surface molecule and IL34, (ii) culturing the lymphocytes under conditions wherein IL34 is secreted, released and specifically captured by the capture moiety, (iii) labelling the IL34 expressing lymphocytes with a label moiety, and (iv) optionally detecting and/or isolating said IL34 expressing lymphocytes which are Foxp3$^+$ Treg cells.

As used herein, the terms "forkhead box P3 (Foxp3$^+$) regulatory T cells" or "Foxp3$^+$ Treg cells" refer to 2-10% of CD4$^+$ and CD8$^+$ T cells in humans and rodents (rats or mice). CD4$^+$ T cells constitutively express CD25, CTLA-4 and GITR, as well as the transcription factor Foxp3, which is involved in their development and function. The characteristic marker of Treg cells is Foxp3.

As used herein, the terms "Interleukin-34" or "IL34" are well known in the art and refer to a cytokine that promotes the proliferation, survival and differentiation of monocytes and macrophages. The naturally occurring human IL-34 protein has an aminoacid sequence of 242 amino acids provided in the UniProt database under accession number Q6ZMJ4. It should be further noted that IL34 is herein defined as including the naturally occurring human polypeptide IL-34 and naturally-occurring allelic variations of the polypeptide (3). Allelic variations are naturally-occurring base changes in the species population which may or may not result in an amino acid change in a polypeptide or protein.

As used herein, the term "biological sample" refers to any body fluid or tissue that contains peripheral blood mononuclear cells "PBMC" or lymphocytes.

As used herein, the term "lymphocytes" refers to a kind of subtypes population of white blood cell in a vertebrate's immune system. Lymphocytes include natural killer cells (NK cells), T cells and B cells. In the context of the invention, lymphocytes T cells are used. Lymphocytes T cells are characterized by the presence of a T-cell receptor (TCR) on the cell surface. As used herein, the term "TCR" has its general meaning in the art and refers to the molecule found on the surface of T cells that is responsible for recognizing antigens bound to MHC molecules. The TCR heterodimer consists of an alpha and beta chain in 95% of T cells, whereas 5% of T cells have TCRs consisting of gamma and delta chains. Each chain of the TCR is a member of the immunoglobulin superfamily and possesses one N-terminal immunoglobulin (Ig)-variable (V) domain, one Ig-constant (C) domain, a transmembrane region, and a short cytoplasmic tail at the C-terminal end. The constant domain of the TCR consists of short connecting sequences in which a cysteine residue forms a disulfide bond, making a link between the two chains. The structure allows the TCR to associate with other molecules like CD3 which possess three distinct chains (γ, δ, and ε) in mammals and the ζ-chain. These accessory molecules have negatively charged transmembrane regions and are vital to propagating the signal from the TCR into the cell.

In a particular embodiment, the lymphocytes are chimeric antigen receptor T Cells (CAR-T Cells). As used herein, the term "Chimeric Antigen Receptor T Cells" also called CAR-T Cells or CAR modified T cells refers to lymphocytes which express Chimeric Antigen Receptor (CAR). The term "Chimeric Antigen Receptor" or "CAR" has its general meaning in the art and refers to an artificially constructed hybrid protein or polypeptide containing the antigen binding domains of an antibody (e.g., scFv) linked to T-cell signaling domains. Characteristics of CARs include their ability to redirect T-cell specificity and reactivity toward a selected target in a non-MHC-restricted manner, exploiting the antigen-binding properties of monoclonal antibodies. The non-MHC-restricted antigen recognition gives T cells expressing CARs the ability to recognize antigen independently of antigen processing, thus bypassing a major mechanism of tumor escape. Moreover, when expressed in T-cells, CARs advantageously do not dimerize with endogenous T cell receptor (TCR) alpha and beta chains. Strategies to design and produce such CARs are well known in the art, references can be found for example in Bonini and Mondino, Eur. J. Immunol. 2015 (19), Srivastava and Riddell, Trends Immunol. 2015 (20), Jensen and Riddell, Curr. Opin. Immunol. 2015 (21), Gill and June, Immunol. Rev. 2015 (22). In a particular embodiment, CAR-T cells comprises an antigen-binding domain comprising, consisting of, or consisting essentially of, a single chain variable fragment (scFv). In some embodiments, the antigen binding domain comprises a linker peptide. The linker peptide may be positioned between the light chain variable region and the heavy chain variable region.

Within the context of the invention, a "PBMC or lymphocyte containing fluid" encompasses blood (whole blood sample, serum sample, or plasma sample) and synovial fluid.

A "lymphocyte containing tissue" encompasses spleen, thymus, lymph nodes, bone marrow, Peyer's patches, and tonsils.

In one embodiment, the biological sample is any sample which may be obtained from a patient for the purpose of in vitro evaluation or ex vivo approach.

A preferred biological sample is a blood sample (e.g. whole blood sample, serum sample, or plasma sample), more particularly a blood sample obtained from a transplanted patient or a patient suffering from an autoimmune disease, allergy or cancer.

Means for Capturing the Foxp3$^+$ Treg Cells of the Invention

The means of capture comprise a capture moiety which has been anchored to the cell surface by a means suitable for the cell to be sorted.

The capture moiety may be coupled to the anchoring means (the "anchor moiety") optionally through a linking moiety, and may also include a linking moiety which multiplies the number of capture moieties available and thus the potential for capture of product, such as branched polymers, including, for example, modified dextran molecules, polyethylene glycol, polypropylene glycol, polyvinyl alcohol, and polyvinylpyrrolidone.

Examples of suitable cell surface molecules include, but are not limited to, any molecule associated with the cell surface. Suitable molecules include, but are not limited to, cell surface markers such as CD45 (pan leukocyte), CD3 (T cells (activating)), CD4, CD8, and other CD markers or cell adhesion molecules.

In one embodiment, the cell surface molecule is selected from the group consisting of CD3, CD4, CD8 and CD45.

Alternatively, the capture moiety specifically binds to cell surface molecules such as the MHC antigens or glycoproteins, could also be used.

In some embodiments, the capture moiety binds specifically to a TCR or to a chimeric antigen receptor.

Specific binding partners include capture moieties and label moieties. The capture moieties are those which attach both to the cell, either directly or indirectly, and the product. The label moieties are those which attach to the product and may be directly or indirectly labeled. Specific binding partners include any moiety for which there is a relatively high affinity and specificity between product and its binding partner, and in which the dissociation of the product: partner complex is relatively slow so that the product: partner complex is detected during the labeling or cell separation technique.

Specific binding partners may include, but are not limited to, substrates or substrate analogs to which a product will bind. These substrates include, but are not limited to, peptides, polysaccharides, steroids, biotin, digitoxin, digitonin, and other molecules able to bind the secreted product, and in a preferred embodiment will include antibodies.

When the capture moiety is an antibody it may be referred to as the "capture antibody" or "catch antibody." As used herein, the term "antibody is intended to include polyclonal and monoclonal antibodies, chimeric antibodies, single domains antibodies, haptens and antibody fragments, bispecific antibodies, trispecific antibodies and molecules which are antibody equivalents in that they specifically bind to an epitope on the product antigen.

Bispecific antibodies, also known as bifunctional antibodies, have at least one antigen recognition site for a first antigen and at least one antigen recognition site for a second antigen. Such antibodies can be produced by recombinant DNA methods or chemically by methods known in the art. Chemically created bispecific antibodies include but are not limited to antibodies that have been reduced and reformed so as to retain their bivalent characteristics and antibodies that have been chemically coupled so that they have at least two antigen recognition sites for each antigen.

Bispecific antibodies include all antibodies or conjugates of antibodies, or polymeric forms of antibodies which are capable of recognizing two different antigens. Antibodies can be immobilized on a polymer or particle.

In one embodiment, the capture moiety is selected from the group consisting of a bispecific antibody which binds to CD3 and IL34, a bispecific antibody which binds to CD4 and IL34, a bispecific antibody which binds to CD8 and IL34, a bispecific antibody which binds to CD45 and IL34, a bispecific antibody which binds to a TCR and IL34, and a bispecific antibody which binds to a chimeric antigen receptor and IL34.

Trispecific antibodies have at least one antigen recognition site for a first antigen, at least one antigen recognition site for a second antigen and at least one antigen recognition site for a third antigen.

Trispecific antibodies include all antibodies or conjugates of antibodies, or polymeric forms of antibodies which are capable of recognizing three different antigens. Antibodies can be immobilized on a polymer or particle.

The capture moiety binds to IL34 and to other cytokines such as IFNγ, IL10 and MCSF.

Accordingly, in a particular embodiment, the capture moiety is selected from the group consisting of a trispecific antibody which binds to IL34, IFNγ and CD3, a trispecific antibody which binds to IL34, IL10 and CD3, a trispecific antibody which binds to IL34, MCSF and CD3, and a trispecific antibody which binds to IL34, CD3 and an antigen.

As used herein, the term "antigen" refers a compound that can elicit an immune response. In the context of the invention, the antigen (e.g MHC antigens or glycoproteins) allows to recruit Foxp3+ Treg cells in an environment of interest.

In the practice of the invention, the capture moiety can be attached to a cell membrane (or cell wall) by a variety of methods. Suitable methods include, but are not limited to, direct chemical coupling to amino groups of the protein components; coupling to thiols (formed after reduction of disulfide bridges) of the protein components; indirect coupling through antibodies (including pairs of antibodies) or lectins; anchoring in the lipid bilayer by means of a hydrophobic anchor moiety; and binding to the negatively charged cell surface by polycations.

In other embodiments of the invention, the capture moiety is introduced using two or more steps, e.g., by labeling the cells with at least one anchor moiety which allows the coupling of the capture moiety to the anchor moiety either directly for instance by a biotin/avidin complex or indirectly through a suitable linking moiety or moieties.

Methods for direct chemical coupling of antibodies to the cell surface are known in the art, and include, for example, coupling using glutaraldehyde or maleimide activated antibodies. Methods for chemical coupling using multiple step procedures include, for example, biotinylation, coupling of TNP or digoxigenin using, for example, succinimide esters of these compounds. Biotinylation may be accomplished by, for example, the use of D-biotinyl-N-hydroxysuccinimide.

Succinimide groups react effectively with amino groups at pH values above 7, and preferentially between about pH 8.0 and about pH 8.5. Biotinylation may also be accomplished by, for example, treating the cells with dithiothreitol (DTT) followed by the addition of biotin maleimide.

Coupling to the cells may also be accomplished using antibodies against cell surface antigens ("markers"). Antibodies generally directed to surface antigens may be required in the range of about 0.1 to 1 µg of antibody per $10^7$ cells, however, this requirement will vary widely in response to the affinity of the antibody to the product and will need to be determined empirically. Such a determination is well within the skill of one in the art. Thus, the appropriate amount of antibody must be determined empirically and is within the skill of one in the art. This allows coupling to specific cells on cell type specific marker expression.

For instance, classes of cells based such as T cells or subsets thereof can be specifically labeled. As a capture moiety, a bispecific antibody may be used which has an antigen recognition site for the cell or an anchor moiety placed thereon, and the product.

A capture moiety, particularly capture antibodies should be selected based on the amount of secreted product. For example, for cells which secrete only a few molecules, a high affinity antibody should be chosen so as to catch most of the secreted molecules.

Alternatively, in the case where the cell secretes many molecules during the incubation time, a lower affinity antibody may be preferred to prevent too early saturation of the catching matrix. Determination of suitable affinities for the level of proteins secreted is empirical and is within the skill of one in the art.

Other methods of coupling capture moieties to the cells are extensively described in the international patent application no WO94/09117.

It is of course contemplated within the embodiments of the invention that linker moieties may be used between the anchor moiety and the capture moiety when the anchor moiety is coupled in any fashion to the cell surface. Thus, for example, an avidin (or streptavidin) biotin linker moiety may link an antibody anchor moiety with a capture moiety. Bispecific antibody systems may also act as linker moieties.

In order to analyze and, if desired, to select cells that have the capability of secreting Interleukin-34 (IL34), cells modified as above to contain the capture moiety are incubated under conditions that allow the production and secretion of the product in a sufficient amount to allow binding to and detection of the cells that contain the captured product. These conditions are known to those of skill in the art and include, inter alia, appropriate temperature, pH, and concentrations of salts, growth factors and substrates in the incubation medium, as well as the appropriate concentrations of gas in the gaseous phase. When it is desirable to distinguish between high and low producer cells, the time of incubation is such that product secretion by the cells is still in a linear phase. The appropriate conditions can be determined empirically and such a determination is within the skill of one in the art. Additionally, secretion by the cells can be modified, that is upregulated, induced, or reduced using a biological modifier. Suitable biological modifiers include, but are not limited to, molecules and other cells. Suitable molecules include, but are not limited to, drugs, cytokines, small molecules, hormones, combinations of interleukins, lectins and other stimulating agents e.g. PMA, ionomycin, LPS, bispecific antibodies and other agents which modify cellular functions or protein expression.

Alternatively, the cells can be pretreated with these agents or cells prior to the incubation step.

In other embodiments, capture moieties that do not contain captured IL34 may be detected. This allows, for example, the isolation of cells that secrete high amounts of IL34 by employing a negative separation method, i.e., detection of cells not highly saturated with IL34. The cells can be labeled with other substances recognizing, including, but not limited to, cell surface markers, cell type, cellular parameters such as DNA content, cell status, or number of capture moieties.

The enumeration of actual capture moieties can be important to compensate for varying amounts of these molecules due to, for example, different conjugation potentials of the cells. It may be especially important for the isolation of rare cells to exclude cells with decreased or increased capability for binding the product capture system, including the anchor and capture moieties.

Means for Labeling the Foxp3$^+$ Treg Cells of the Invention

Analysis of the cell population and cell sorting based upon the presence of the label may be accomplished by a number of techniques known in the art.

Cells can be analyzed or sorted by, for example, flow cytometry or FACS. These techniques allow the analysis and sorting according to one or more parameters of the cells. Usually one or multiple secretion parameters can be analyzed simultaneously in combination with other measurable parameters of the cell, including, but not limited to, cell type, cell surface antigens, DNA content, etc. The data can be analyzed and cells can be sorted using any formula or combination of the measured parameters. Cell sorting and cell analysis methods are known in the art and are described in, for example, THE HANDBOOK OF EXPERIMENTAL IMMUNOLOGY, Volumes 1 to 4, (D. N. Weir, editor) and FLOW CYTOMETRY AND CELL SORTING (A. Radbruch, editor, Springer Verlag, 1992). Cells can also be analyzed using microscopy techniques including, for example, laser scanning microscopy, fluorescence microscopy; techniques such as these may also be used in combination with image analysis systems. Other methods for cell sorting include, for example, panning and separation using affinity techniques, including those techniques using solid supports such as plates, beads and columns.

Some methods for cell sorting utilize magnetic separations, and some of these methods utilize magnetic beads. Different magnetic beads are available from a number of sources, including for example, Miltenyi Biotec GmbH (Germany).

Preferred magnetic labeling methods include colloidal superparamagnetic particles in a size range of 5 to 200 nm, preferably in a size of 10 to 100 nm. These magnetic particles allow a quantitative magnetic labeling of cells, thus the amount of coupled magnetic label is proportional to the amount of bound product, and the magnetic separation methods are sensitive to different amounts of product secretion. Colloidal particles with various specificities are known in the art, and are available, for example, through Miltenyi Biotec GmbH.

The use of immunospecific fluorescent or magnetic liposomes may also be used for quantitative labeling of captured product. In these cases, the liposomes contain magnetic material and/or fluorescent dyes conjugated with antibody on their surfaces, and magnetic separation is used to allow optimal separation between nonproducing, low producing, and high producing cells.

The magnetic separation can be accomplished with high efficiency by combining a second force to the attractive magnetic force, causing a separation based upon the different strengths of the two opposed forces.

Typical opposed forces are, for example, forces induced by magnetic fluids mixed in the separation medium in the magnetic separation chamber, gravity, and viscous forces induced by flow speed of medium relative to the cell.

Any magnetic separation method, preferably magnetic separation methods allows quantitative separation, can be used. It is also contemplated that different separation methods can be combined, for example, magnetic cell sorting can be combined with FACS, to increase the separation quality or to allow sorting by multiple parameters.

Preferred techniques include high gradient magnetic separation (HGMS), a procedure for selectively retaining magnetic materials in a chamber or column disposed in a magnetic field. In one application of this technique the product is labeled by attaching it to a magnetic particle. The attachment is generally through association of the product with a label moiety which is conjugated to a coating on the magnetic particle which provides a functional group for the conjugation. The product associated with the cell and coupled to a magnetic label is suspended in a fluid which is then applied to the chamber. In the presence of a magnetic gradient supplied across the chamber, the magnetically labeled cell is retained in the chamber; if the chamber contains a matrix, it becomes associated with the matrix. Cells which do not have or have only a low amount of magnetic labels pass through the chamber.

The retained cells can then be eluted by changing the strength of, or by eliminating, the magnetic field or by introducing a magnetic fluid. The selectivity for a captured product is supplied by the label moiety conjugated either directly or indirectly to the magnetic particle or by using a primary antibody and a magnetic particle recognizing the primary antibody.

The chamber across which the magnetic field is applied is often provided with a matrix of a material of suitable magnetic susceptibility to induce a high magnetic field gradient locally in the chamber in volumes close to the surface of the matrix. This permits the retention of fairly weakly magnetized particles. Publications describing a variety of HGMS systems are known in the art, and include, for example, U.S. Pat. Nos. 4,452,773, 4,230,685 and 4,770,183.

As seen from above, processes embodied by the invention include the following steps: a. coupling an anchor moiety to the surface of the cells suspected of secreting IL34; b. coupling to the anchor moiety a capture moiety which captures IL34; c. incubating the cells with the coupled capture moiety to allow synthesis and secretion of IL34 under conditions whereby the product binds to the capture moiety; and d. labeling the captured product with a label moiety.

In addition, in other embodiments, the processes include labeling the cells that contain captured product, if any. Other embodiments may also include analyzing the cell population to detect labeled cells, if any, and if desired, sorting the labeled cells, if any.

Selection of the high secretor cells is carried out in multiple rounds. Each separation process involves the use of a cell separation process, i.e., a quantitative magnetic separation system that distinguishes different levels of bound product, or a FACS. The cells having the highest labeling (eventually normalized on a cell to cell basis using further parameters) are sorted and expanded in culture again.

Magnetic and FACS separation can be combined.

FACS sorting is preferentially performed by additionally labeling the cells for amount of capture moiety using a different fluorochrome than that with which the cells are originally labeled, then selecting for cells with a high ratio of amount of product to amount of antibody. Multiple rounds of separation using high cell numbers of $10^7$ to $10^{10}$ cells allows isolation of rare genetic variants showing extraordinarily high levels of production and genetic stability. In order to avoid the selection of cells producing aberrant forms of product, different label moieties may be used during the different rounds of separation.

In one embodiment, the label moiety is a labelled anti-IL34 antibody.

For instance, many different labels that can be conjugated to an antibody are known to the skilled in the art. For example, radioisotopes, e.g. $^{32}P$, $^{35}S$ or $^{3}H$; fluorescence or luminescence markers, e.g. fluorescein (FITC), rhodamine, texas red, phycoerythrin (PE), allophycocyanin, peridinin-chlorophyll-protein complex (PerCP), 6-carboxyfluorescein (6-FAM), 2', 7'-dimethoxy-4', 5'-dichloro-6-carboxyfluorescein (JOE), 6-carboxy-X-rhodamine (ROX), 6-carboxy-2', 4', 7', 4, 7-hexachlorofluorescein (HEX), 5-carboxyfluorescein (5-FAM) or N, N, N', N'-tetramethyl-6-carboxyrhodamine (TAMRA); antibodies or antibody fragments, e.g. F(ab)2 fragment; affinity labels, e.g. biotin, avidin, agarose, bone morphogenetic protein (BMP), matrix bound, haptens; and enzymes or enzyme substrates, e.g. alkaline phosphatase (AP) and horseradish peroxidase (HRP).

The label moiety may be a labeled anti-IL34 antibody, which may include, but is not limited to, fluorescence or luminescence markers, magnetic bead conjugated, colloidal bead conjugated, AMCA, fluorescent particle or liposome conjugated antibodies. Alternatively the label moiety may be any suitable label including but not limited to those described herein.

Kits and Antibodies of the Invention

In another aspect, the invention relates to a kit comprising at least one capture moiety which binds to the cell through a cell surface molecule and to interleukin-34 (IL34) and a label moiety.

The invention also relates to a kit for use in a method of the invention, comprising at least one capture moiety which binds to the cell through a cell surface molecule and to interleukin-34 (IL34) and a label moiety.

In one embodiment, the capture moiety which binds to the cell through a cell surface molecule and to interleukin-34 (IL34) is selected from the group consisting of a bispecific antibody which binds to CD3 and IL34, a bispecific antibody which binds to CD4 and IL34, a bispecific antibody which binds to CD8 and IL34, a bispecific antibody which binds to CD45 and IL34, a bispecific antibody which binds to a TCR and IL34, and a bispecific antibody which binds to a chimeric antigen receptor and IL34.

In a preferred embodiment, the kit comprises a bispecific antibody which binds to CD4 and IL34, a bispecific antibody which binds to CD8 and IL34, a bispecific antibody which binds to a TCR and IL34, and a bispecific antibody which binds to a chimeric antigen receptor and IL34.

In one embodiment, the capture moiety which binds to the cell through a cell surface molecule and to interleukin-34 (IL34) is selected from the group consisting of a trispecific antibody which binds to Il34, IFNγ and CD3, a trispecific antibody which binds to Il34, IL10 and CD3, a trispecific antibody which binds to IL34, MCSF and CD3, and a trispecific antibody which binds to IL34, CD3 and an antigen.

In a particular embodiment, the kit comprises a trispecific antibody which binds to Il34, IFNγ and CD3, a trispecific antibody which binds to Il34, IL10 and CD3, a trispecific antibody which binds to IL34, MCSF and CD3, and a trispecific antibody which binds to IL34, CD3 and an antigen.

In one embodiment, the label moiety is a labeled anti-IL34 antibody.

Optionally, the kit may include physiologically acceptable buffer. Such buffers are known in the art and include, but are not limited to, PBS with and without BSA, isotonic saline, cell culture media and any special medium required by the particular cell type. Buffers might be used that reduce cross-labeling and increase the local IL-34 concentration around the cells. Buffers may include agents for increasing viscosity or decreasing permeability. Suitable agents are described herein. The viscosity of the medium can be reduced before analysis by any method known in the art including, but not limited to, dissolution in a physiologically acceptable buffer, dissolving heat, EDTA, and enzymes. In the absence of added medium cells already suspended in a medium may be directly added to the vial.

Additional structures may be added for catching unbound IL34 to reduce cell cross-contamination thereby reducing the diffusion of products away from the producing cells. These include, but are not limited to, anti-IL34 antibody immobilized to gel elements, beads, magnetic beads, polymers.

Biological modifiers may also be added to the buffer or medium to induce specific secretion.

Additional label moieties such as antibodies (magnetically or fluorescently labeled) are also present, including, but not limited to anti-cell surface antibodies to identify cell types, propidium iodide to label dead cells, and magnetic beads to label certain cell types.

All materials can be placed in a single container such as a vial and the cell sample added. The contents are incubated to allow secretion of a product and subsequent capture of the product and binding of the label moiety to the product. The cells which have secreted and bound IL34 can then be separated and/or analyzed based on the presence, absence or amount of the captured IL34.

In another further aspect, the invention relates to a bispecific antibody selected from the group consisting of a bispecific antibody which binds to CD3 and IL34, a bispecific antibody which binds to CD4 and IL34, a bispecific antibody which binds to CD8 and IL34, a bispecific antibody which binds to CD45 and IL34, a bispecific antibody which binds to a TCR and IL34, and a bispecific antibody which binds to a chimeric antigen receptor and IL34.

In a another further aspect, the invention relates to a trispecific antibody selected from the group consisting of a trispecific antibody which binds to Il34, IFNγ and CD3, a trispecific antibody which binds to Il34, IL10 and CD3, a trispecific antibody which binds to IL34, MCSF and CD3, and a trispecific antibody which binds to IL34, CD3 and an antigen.

Furthermore, such isolated and optionally expanded population of Foxp3$^+$ Treg cells is of interest in the fields of autoimmunity, allergy, transplantation, treatment with therapeutic protein and gene therapy, to avoid degradation of self or therapeutic molecules/tissues by the immune system. Indeed, said population of Foxp3$^+$ Treg cells may be expanded and pulsed with antigens of interest in order to efficiently induce antigen-specific immune tolerance.

Populations of Foxp3$^+$ Treg Cells according to a Method of the Invention and Pharmaceutical Compositions Comprising Them In another aspect, the invention also relates to a population of Foxp3$^+$ Treg cells obtainable by a method as defined above.

In one embodiment, the population of Foxp3$^+$ Treg cells obtainable by a method as defined above is an isolated population of CD4$^+$ Foxp3$^+$ Tregs.

In another embodiment, the population of Foxp3$^+$ Treg cells obtainable by a method as defined above is an isolated population of CD8$^+$ Foxp3$^+$ Tregs.

In another embodiment, the population of Foxp3$^+$ Treg cells obtainable by a method as defined above is an isolated population of CD4$^+$ Foxp3$^+$ Tregs and CD8$^+$Foxp3$^+$ Tregs.

Once a population of Foxp3$^+$ Treg cells (CD4$^+$ Foxp3$^+$ Tregs and/or CD8$^+$ Foxp3$^+$ Tregs) have been isolated from a mammalian, such as a rodent (e.g. a mouse or a rat), a feline, a canine or a primate (including human subject), such population of interest may be expanded.

As used herein, the terms "expand" and "expansion" refers to increasing in number, as in an increase in the number of regulatory T cells. In one embodiment, the regulatory T cells that are expanded ex vivo increase in number relative to the number originally present in the culture. In another embodiment, the regulatory T cells that are expanded ex vivo increase in number relative to other cell types in the culture. The term "ex vivo" as used herein, refers to cells that have been removed from a living organism, (e.g., a human) and propagated outside the organism (e.g., in a culture dish, test tube, or bioreactor).

Such step of expansion may be carried out by culturing the isolated population of Foxp3$^+$ Treg cells with compounds (e.g., IL-2) are added to the culture medium to enhance or promote Treg expansion and/or activation and/or survival of the cells.

Within the context of the invention, the isolated population of Foxp3$^+$ Treg cells, expanded or not, may be then pulsed with an antigen of interest in order to achieve a population of antigen-specific Foxp3$^+$ Treg cells, said antigen being provided in an amount effective to "prime" the isolated population of Foxp3$^+$ Treg cells and thus obtain a population of Foxp3$^+$ Treg cells specific for said antigen. Indeed such antigen-specific Foxp3$^+$ Treg cells are useful in the prevention or treatment of unwanted immune responses, such as those involved in autoimmune disorders, immune reactions to therapeutic proteins, and/or allergies.

Accordingly, populations of Foxp3$^+$ Treg cells specific for an antigen associated with the disease to be treated (pathogenic antigen) should be obtained. Therefore, the antigen of interest is selected from the group consisting of autoantigens, allo-antigens and allergens.

Thus, when the autoimmune disease is multiple sclerosis, the autoantigen is selected from the group consisting of myelin-related antigens (e.g. myelin basic protein (MBP) (e.g. MBP83-102 peptide), myelin oligodendrocyte glycoprotein (MOG) (e.g. MOG35-55 peptide) and proteolipid protein (PLP) (e.g. PLP139-151 peptide). When the autoimmune disease is Type I diabetes (T1D), the autoantigen is selected from the group consisting of insulin, insulin precursor proinsulin (ProIns), glutamic acid decarboxylase 65 (GAD65), glial fibrillary acidic protein (GFAP), islet-specific glucose-6-phosphatase catalytic subunit-related protein (IGRP), insulinoma-associated antigen-2 (IA-2) and zinc transporter 8 (ZnT8). When the autoimmune disease is rheumatoid arthritis, the autoantigen is type II collagen (CTII).

It is also intended that alloantigens include, but are not limited to, antigens expressed by the allograft, proteins expressed in the course of gene therapy (and also viral antigens issued from the viral vector used) as well as therapeutic proteins.

As such an "allograft" is a transplant between two individuals of the same species having two genetically different MHC haplotypes.

The term "therapeutic proteins" refers to proteins or peptides and their administration in the therapy of any given condition or illness. Therapeutic proteins relate to any protein or peptide, such as therapeutic antibodies, cytokines, enzymes or any other protein, that is administered to a patient. Examples of protein therapy relate to treatment of hemophilia via administration of plasma-derived or recombinant clotting factor concentrates (e.g. factor VIII and factor IX), the treatment of cancer or cardiovascular disease using monoclonal antibodies or the treatment of metabolic or lysosomal disease by enzyme replacement therapy.

In another aspect, the invention relates to a method for obtaining a population of antigen-specific Foxp3$^+$ Treg cells comprising the steps of: (i) culturing the population of Foxp3$^+$ Treg cells with a culture medium comprising an amount of antigen of interest; and (ii) isolating the population of antigen-specific Foxp3$^+$ Treg cells.

As used herein, the term "culture medium" refers to any medium capable of supporting the growth and the differentiation of Foxp3$^+$ Treg cells. Typically, it consists of a base medium containing nutrients (a source of carbon, aminoacids), a pH buffer and salts, which can be supplemented with growth factors and/or antibiotics. Typically, the base medium can be RPMI 1640 or DMEM which are commercially available standard media.

In one embodiment, the culture medium may comprise a mixture of several antigens (involved in the disease to be treated). For instance, when the disease to be prevented or to be treated is graft rejection, the culture medium may comprise a lysate from the graft to be transplanted to the patient. When the disease to be prevented or to be treated is multiple sclerosis, the culture medium may comprise a mixture of myelin-related antigens (e.g. myelin basic protein (MBP) (e.g. MBP83-102 peptide), myelin oligodendrocyte glycoprotein (MOG) (e.g. MOG35-55 peptide) and proteolipid protein (PLP) (e.g. PLP139-151 peptide).

Typically, the culture of a population of Foxp3$^+$ Treg cells with the culture medium shall be carried from 3, 6, 12 hours to 1 day or more.

The invention also provides a pharmaceutical composition comprising the population of Foxp3+ Treg cells according to the invention. The pharmaceutical composition may generally include one or more pharmaceutically acceptable and/or approved carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycollic acids, polymeric amino acids, amino acid copolymers, lipid aggregates, or the like. This pharmaceutical composition can contain additional additives such as mannitol, dextran, sugar, glycine, lactose or polyvinylpyrrolidone or other additives such as antioxidants or inert gas, stabilizers or recombinant proteins (e. g. human serum albumin) suitable for in vivo administration.

As used herein, the term "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Therapeutic Methods and Uses of Foxp3$^+$ Treg Cells

As above-mentioned, a population of Foxp3$^+$ Treg cells of the invention is of interest in the fields of autoimmunity, allergy, transplantation, gene therapy and treatment with therapeutic protein, to avoid degradation of self-tissues or therapeutic proteins by the immune system. A population of Foxp3$^+$ Treg cells according to the invention indeed exhibits the ability to induce immune tolerance and/or to suppress and/or inhibit immune responses, preferably antigen-specific immune response(s) directed against the antigen(s) involved in the disease to be treated, and/or unwanted adaptive immune responses mediated by CD4$^+$ T cells, CD8$^+$ T cells, preferably immune T-cell tolerance or reduced T-cell activation.

Another aspect of the invention thus relates to a population of Foxp3$^+$ Treg cells of the invention for use as a medicament.

The population of Foxp3+ Treg cells primed or not may be reintroduced to the patient by a number of approaches. Preferably, they are injected intravenously. In one embodiment, about $1 \times 10^4$ to about $1 \times 10^8$ cells are reintroduced to the patient.

In one embodiment, the invention relates to a population of Foxp3$^+$ Treg cells of the invention for use in a method for preventing or treating an autoimmune disease.

The invention also relates to a method for preventing or treating an autoimmune disease comprising the step of administering a pharmaceutically effective amount of a population of Foxp3+ Treg cells to a patient in need thereof.

As used herein, the term "autoimmune disease" refers to a disease in which the immune system produces an immune response (for example, a B-cell or a T-cell response) against an antigen that is part of the normal host (that is an auto-antigen), with consequent injury to tissues. In an autoimmune disease, the immune system of the host fails to recognize a particular antigen as "self" and an immune reaction is mounted against the host's tissues expressing the antigen.

Exemplary autoimmune diseases affecting humans include rheumatoid arthritis, juvenile oligoarthritis, collagen-induced arthritis, adjuvant-induced arthritis, Sjogren's syndrome, multiple sclerosis, experimental autoimmune encephalomyelitis, inflammatory bowel disease (for example, Crohn's disease and ulcerative colitis), autoimmune gastric atrophy, pemphigus vulgaris, psoriasis, vitiligo, type 1 diabetes, non-obese diabetes, myasthenia gravis, Grave's disease, Hashimoto's thyroiditis, sclerosing cholangitis, sclerosing sialadenitis, systemic lupus erythematosis, autoimmune thrombocytopenia purpura, Goodpasture's syndrome, Addison's disease, systemic sclerosis, polymyositis, dermatomyositis, acquired hemophilia, thrombotic thrombocytopenic purpura and the like.

In another embodiment, the invention relates to a population of Foxp3$^+$ Treg cells of the invention for use in a method for preventing or treating graft rejection (or for inducing transplant tolerance).

The invention also relates to a method for preventing or treating graft rejection (or inducing transplant tolerance) comprising the step of administering a pharmaceutically effective amount of a population of Foxp3+ Treg cells of the invention to a patient in need thereof.

As used herein, the term "transplant rejection" encompasses both acute and chronic transplant rejection. "Acute rejection" is the rejection by the immune system of a tissue transplant recipient when the transplanted tissue is immunologically foreign. Acute rejection is characterized by infiltration of the transplant tissue by immune cells of the recipient, which carry out their effector function and destroy the transplant tissue. The onset of acute rejection is rapid and generally occurs in humans within a few weeks after transplant surgery. Generally, acute rejection can be inhibited or suppressed with immunosuppressive drugs such as rapamycin, cyclosporin, anti-CD40L monoclonal antibody and the like. "Chronic transplant rejection" generally occurs in humans within several months to years after engraftment, even in the presence of successful immunosuppression of acute rejection. Fibrosis is a common factor in chronic rejection of all types of organ transplants.

The term "transplantation" and variations thereof refers to the insertion of a transplant (also called graft) into a recipient, whether the transplantation is syngeneic (where the donor and recipient are genetically identical), allogeneic (where the donor and recipient are of different genetic origins but of the same species), or xenogeneic (where the donor and recipient are from different species). Thus, in a typical scenario, the host is human and the graft is an isograft, derived from a human of the same or different genetic origins. In another scenario, the graft is derived from a species different from that into which it is transplanted, including animals from phylogenically widely separated species, for example, a baboon heart being transplanted into a human host.

In one embodiment the donor of the transplant is a human. The donor of the transplant can be a living donor or a deceased donor, namely a cadaveric donor.

In one embodiment, the transplant is an organ, a tissue, or cells.

As used herein, the term "organ" refers to a solid vascularized organ that performs a specific function or group of functions within an organism. The term organ includes, but is not limited to, heart, lung, kidney, liver, pancreas, skin, uterus, bone, cartilage, small or large bowel, bladder, brain, breast, blood vessels, esophagus, fallopian tube, gallbladder, ovaries, pancreas, prostate, placenta, spinal cord, limb including upper and lower, spleen, stomach, testes, thymus, thyroid, trachea, ureter, urethra, uterus. As used herein, the term "tissue" refers to any type of tissue in human or animals, and includes, but is not limited to, vascular tissue, skin tissue, hepatic tissue, pancreatic tissue, neural tissue, urogenital tissue, gastrointestinal tissue, skeletal tissue including bone and cartilage, adipose tissue, connective tissue including tendons and ligaments, amniotic tissue, chorionic tissue, dura, pericardia, muscle tissue, glandular tissue, facial tissue, ophthalmic tissue.

In a particular embodiment, the transplant rejection is cardiac allotransplant rejection.

As used herein, the term "cells" refers to a composition enriched for cells of interest, preferably a composition comprising at least 30%, preferably at least 50%, even more preferably at least 65% of said cells.

In certain embodiments the cells are selected from the group consisting of multipotent hematopoietic stem cells derived from bone marrow, peripheral blood, or umbilical cord blood; or pluripotent (i.e. embryonic stem cells (ES) or induced pluripotent stem cells (iPS)) or multipotent stem cell-derived differentiated cells of different cell lineages such as cardiomyocytes, beta-pancreatic cells, hepatocytes, neurons, etc. . . .

In one embodiment, the cell composition is used for allogeneic hematopoietic stem cell transplantation (HSCT) and thus comprises multipotent hematopoietic stem cells, usually derived from bone marrow, peripheral blood, or umbilical cord blood.

HSCT can be curative for patients with leukemia and lymphomas. However, an important limitation of allogeneic HCT is the development of graft versus host disease (GVHD), which occurs in a severe form in about 30-50% of humans who receive this therapy.

In another embodiment, the invention relates to a population of Foxp3$^+$ Treg cells of the invention for use in a method for preventing or treating any unwanted immune reaction against a therapeutic protein.

As used herein, the term "unwanted immune response against a therapeutic protein" refers to any unwanted immune reaction directed to proteins expressed in the course of gene therapy, and/or therapeutic proteins, such as factor VIII (hemophilia A) and other coagulation factors, enzyme replacement therapies, monoclonal antibodies (e.g. natalizumab, rituximab, infliximab), polyclonal antibodies, enzymes or cytokines (e.g. IFNβ).

In another embodiment, the invention relates to a population of Foxp3$^+$ Treg cells of the invention for use in the prevention or the treatment of allergy.

As used herein, the term "allergy" or "allergies" refers to a disorder (or improper reaction) of the immune system. Allergic reactions occur to normally harmless environmental substances known as allergens; these reactions are acquired, predictable, and rapid. Strictly, allergy is one of four forms of hypersensitivity and is called type I (or immediate) hypersensitivity. It is characterized by excessive activation of certain white blood cells called mast cells and basophils by a type of antibody known as IgE, resulting in an extreme inflammatory response. Common allergic reactions include eczema, hives, hay fever, asthma, food allergies, and reactions to the venom of stinging insects such as wasps and bees.

Uses of the Capture Moiety in Vitro and in Vivo

In another aspect, the invention relates to a method for depleting Foxp3+ Treg cells by using the capture moiety.

Typically, the capture moiety as described above could be conjugated with a cytotoxic agent which is able to deplete Foxp3+ Treg cells.

The term "cytotoxic agent" as used herein refers to a substance that inhibits or prevents the function of cells and/or causes destruction of Foxp3+ Treg cells. A "growth inhibitory agent" when used herein refers to a compound or composition which inhibits growth of a cell, especially Foxp3$^+$ Treg cells, either in vitro or in vivo. Typically, cytotoxic agent or a growth inhibitory agent may be a toxin, radioisotope or label. Examples of growth inhibitory agents include agents that block cell cycle progression, such as agents that induce G1 arrest and M-phase arrest. Typically capture moieties are conjugated to a cytotoxic agent via a linker. In some embodiments, the cytotoxic or cytostatic agent is auristatin E (also known in the art as dolastatin-10) or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP (dimethylvaline-valine-dolaisoleuine-dolaproine-phenylalanine-p-phenylenediamine), MMAF (dovaline-valine-dolaisoleunine-dolaproine-phenylalanine), and MAE (monomethyl auristatin E). The synthesis and structure of auristatin E and its derivatives are described in U.S. Patent Application Publication No. 20030083263; International Patent Publication Nos. WO 2002/088172 and WO 2004/010957; and U.S. Pat. Nos. 6,884,869; 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

In a particular embodiment, the capture moiety as described above could be used to treat a subject suffering from a cancer.

As used herein, the term "cancer" also called "tumor" refers to an abnormal cell growth with the potential to invade or spread to other parts of the body. Cancers including but not limited to breast; colon; rectum; lung; oropharynx; hypopharynx; esophagus; stomach; pancreas; liver; gallbladder; bile ducts; small intestine; urinary tract including kidney, bladder, and urothelium; female genital tract including cervix, uterus, ovaries (e.g., choriocarcinoma and gestational trophoblastic disease); male genital tract including prostate, seminal vesicles, testes and germ cell tumors; endocrine glands including thyroid, adrenal, and pituitary; skin (e.g., hemangiomas and melanomas), bone or soft tissues; blood vessels (e.g., Kaposi's sarcoma); brain, nerves, eyes, and meninges (e.g., astrocytomas, gliomas, glioblastomas, retinoblastomas, neuromas, neuroblastomas, Schwannomas and meningiomas). The terms "cancer and "tumor" also encompass solid tumors arising from hematopoietic malignancies such as leukemias, including chloromas, plasmacytomas, plaques and tumors of mycosis fungoides and cutaneous T-cell lymphoma/leukemia, and lymphomas including both Hodgkin's and non-Hodgkin's lymphomas. As used herein, the terms "cancer and "tumor" are also intended to refer to multicellular tumors as well as individual neoplastic or pre-neoplastic cells. In some embodiments, a tumor is an adenoma and/or an adenocarcinoma. In some embodiments a tumor is a lung adenoma and/or adenocarcinoma.

In another aspect, the invention relates to a method for tracking Foxp3+ Treg cells. The capture moiety as described above could be radiolabelled which is suitable for tracking Foxp3+ Treg cells in vitro or in vivo. Typically, said capture moiety radiolabelled could be used in planar scintigraphy (PS), Positron Emission Tomography (PET), Single Photon Emission Computed Tomography (SPECT), an hybrid of SPECT and/or PET, /CT or their combinations.

In a particular embodiment, the capture moiety could be conjugated with a fluorescent probe (e.g. fluoresceine).

Prognostic Methods of the Invention

In another aspect, the invention relates to an in vitro method for determining whether a patient is at risk of transplant rejection, autoimmune diseases, unwanted immune response against therapeutic proteins or allergies (as above-defined), comprising a step of determining the presence of Foxp3+ Treg cells in a biological sample obtained from said patient by a method of the invention, wherein the presence of Foxp3+ Treg cells is indicative of a reduced risk of transplant rejection, autoimmune diseases, unwanted immune response against therapeutic proteins or allergies.

As used herein, the term "risk" refers to the probability that an event will occur over a specific time period, such as the onset of transplant rejection, and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a patient compared either to the absolute risks of low risk cohorts or an average population risk, which can vary by how clinical risk factors are assessed. Odds ratios, the proportion of positive events to negative events for a given test result, are also commonly used (odds are according to the formula p/(1-p) where p is the probability of event and (1-p) is the probability of no event).

"Risk determination" in the context of the invention encompasses making a prediction of the probability, odds, or likelihood that an event may occur. Risk determination can also comprise prediction of future clinical parameters, traditional laboratory risk factor values, such age, sex mismatch, HLA-testing, etc. . . . ; either in absolute or relative terms in reference to a previously measured population. The methods of the invention may be used to make categorical measurements of the risk of transplant rejection, thus defining the risk spectrum of a category of transplanted patient defined as being at risk of transplant rejection.

As used herein, the term "determining the presence" includes qualitative and/or quantitative detection (i.e. detecting and/or measuring the presence) with or without reference to a control or a predetermined value. As used herein, "detecting" means determining if Foxp3+ Treg cells are present or not in a biological sample and "measuring" means determining the amount of Foxp3+ Treg cells in a biological sample.

As used herein, the term "biological sample" has its general meaning in the art and refers to any sample which may be obtained from a patient for the purpose of in vitro evaluation. A preferred biological sample is a blood sample (e.g. whole blood sample, serum sample, or plasma sample).

In still another aspect, the invention relates to an in vitro method for determining whether a transplanted patient (recipient) is tolerant, comprising a step of determining the presence Foxp3+ Treg cells in a biological sample obtained from said transplanted patient by a method of the invention, wherein the presence of Foxp3+ Treg cells is indicative of tolerance.

As used herein, the terms "tolerance" or "immune tolerance" refers to a state of unresponsiveness of the immune system to substances or tissues that have the capacity to elicit an immune response. As used herein, the term "immune response" includes T cell mediated and/or B cell mediated immune responses. Exemplary immune responses include T cell responses, e.g., cytokine production and cellular cytotoxicity, in addition, the term immune response includes immune responses that are indirectly effected by T cell activation, e.g., antibody production (humoral responses) and activation of cytokine responsive cells, e.g., macrophages. Immune cells involved in the immune response include lymphocytes, such as B cells and T cells (CD4+, CD8+, Th1 and Th2 cells); antigen presenting cells (e.g. professional antigen presenting cells such as dendritic cells); natural killer cells; myeloid cells, such as macrophages, eosinophils, mast cells, basophils, and granulocytes.

Foxp3+ Treg could inhibit lymphocytes conventional which are present in the tumor microenvironment (infiltrating lymphocytes=TILs) and thus these population participates to the cell proliferation and metastasis. It will thus be interesting to detect the presence of Foxp3+ Treg population for determining the prognosis of a subject suffering from a cancer.

Accordingly, the present invention also relates to an in vitro method for predicting the survival time of a subject suffering from a cancer comprising the steps of i) determining the presence Foxp3+ Treg cells in a biological sample obtained from said subject by a method of the invention, and ii) concluding that the presence of Foxp3+ Treg cells is indicative of a poor prognosis (i.e short survival time).

The invention will be further illustrated by the following figures and examples. However, these examples and figures should not be interpreted in any way as limiting the scope of the present invention.

FIGURES

FIG. 1: IL34 is a human Foxp3+Treg-specific cytokine that can inhibit anti-donor immune responses. The percentage of IL34 positive cells was evaluated in healthy individuals among CD4+ or CD8+ CD45RC$^{low}$ or CD45RC$^{high}$ T cells (A) or among Foxp3+ vs Foxp3− CD45RC$^{low}$ CD8+ or CD4+ T cells (B). The mean+/− SEM of 27 healthy individuals was represented (A). A representative plot of 10 healthy individuals was shown (B). (C) The panel show results for the mean+/− SEM of percentage of expression of IL34 in Foxp3$^+$CD45RC$^{low}$CD4$^+$ or CD8$^+$ T cells in healthy individuals.

EXAMPLE

Interleukin-34, a New Role in Regulatory T Cell Immunoregulation and Transplant Tolerance Material & Methods Healthy Volunteers Blood Collection and PBMC Separation.

Blood were collected from healthy donors, after informed consent was given, at the Etablissement Français du Sang (Nantes, France). Blood was diluted 2-fold with PBS before PBMC were isolated by Ficoll-Paque density-gradient centrifugation (Eurobio, Courtaboeuf, France) at 2000 rpm for 20 at room temperature without braking. Collected PBMC were washed in 50 mL PBS at 1800 rpm for 10 min and remaining red cells and platelets are eliminated after incubation 5 min in an hypotonic solution and centrifugation at 1000 rpm for 10 min. Total PBMC were then stimulated with PMA (50 ng/ml) and ionomycin (1 µg/ml) for 7 h in presence of brefeldin A (10 µg/ml) during the last 4 h for FACS analysis of IL34 expression in Tregs. For culture assay, CD3$^+$CD4$^+$CD25$^−$ cells were sorted by FACS Aria after enrichment in CD14$^−$ CD16$^−$ and CD19$^−$ cells by negative selection. Allogeneic APCs used to stimulate effector cells in MLR were obtained by CD3$^+$ cells depletion and 35 Gray irradiation.

Monoclonal Antibodies and Flow Cytometry.

Human antibodies against CD3-PeCy7 (SKY7), CD4-PercPCy5.5 (L200), CD25-APCCy7 (M-A251), CD45RC-FITC (MT2), Foxp3-APC (236A/E7) and IL34-PE (578416, R&D) were used to characterize cell's phenotype. Fluorescence was measured with a Canto II cytometer (BD Biosciences, Mountain View, Calif.), and the FLOWJO software (Tree Star, Inc. USA) was used to analyze data. Cells were first gated by their morphology excluding dead cells by selecting DAPI viable cells.

Statistical Analysis.

Mann Whitney test was used for PBMC phenotype analysis.

Results

IL34 is Expressed by Human T Cells and Possessed a Strong Suppressive Potential.

Figure 1B:
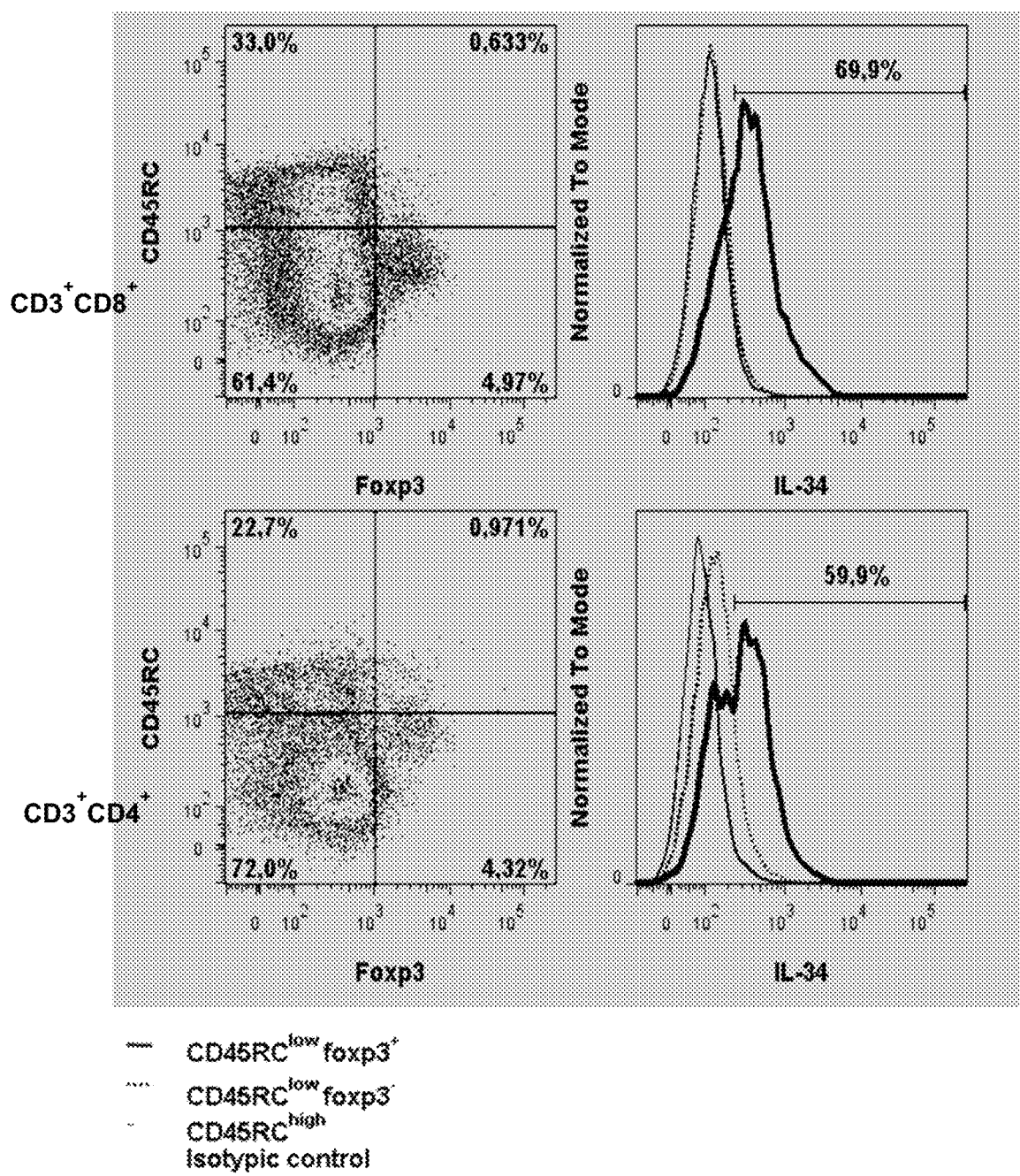
Figure 1C:
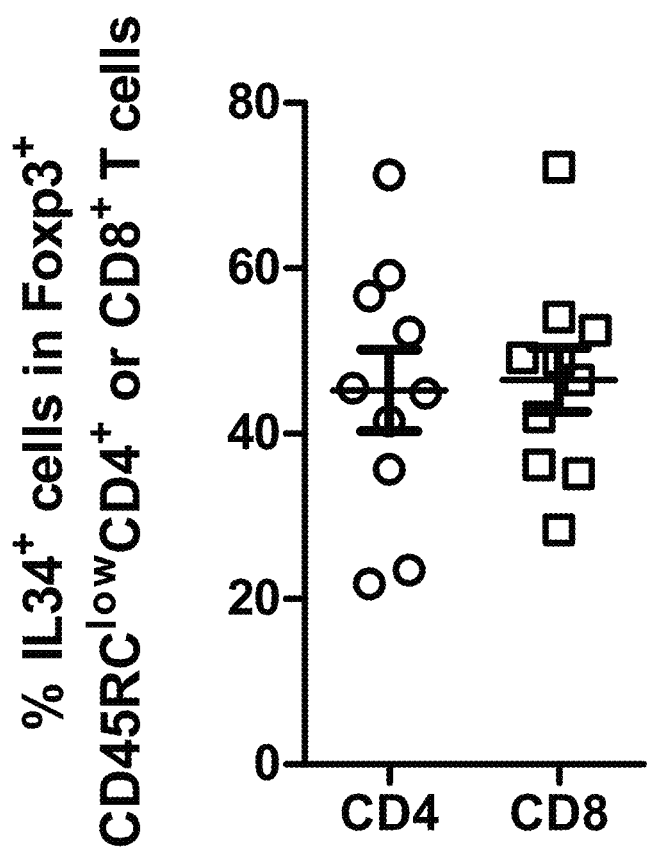

IL34 has never been demonstrated as being expressed by Tregs and inhibiting anti-donor immune responses in human, we wanted to assess the potential and applicability of our findings in human. It has been suggested in the literature that human CD45RC$^{low}$ T cells were associated to Tregs while CD45RC$^{high}$ T cells were associated to naive and effector T cells (4, 5). We first analyzed the IL34 protein expression on CD8$^+$ and CD4$^+$ CD45RC$^{low}$ vs CD45RC$^{high}$ T cells by multicolor flow cytometry (FIG. 1A). Interestingly, we observed that both human CD4$^+$ and CD8$^+$ T cells expressed significant amount of IL34 protein in contrast to CD45RC$^{high}$ T cells. Moreover, we observed that CD8$^+$ T cells expressed slightlymore IL34 than CD4$^+$ T cells. To discriminate IL34 expression by Tregs inside the CD45RC$^{low}$ cells, we analyzed IL34 expression within Foxp3$^+$ Tregs (FIG. 1B). Strikingly, we observed that IL34 expression was specific of CD4$^+$Foxp3$^+$ and CD8$^+$Foxp3$^+$ Tregs versus CD4$^+$Foxp3$^−$, CD8$^+$Foxp3$^−$, CD4$^+$CD45RC$^{high}$ and CD8$^+$CD45RC$^{high}$ T cells subsets, indicating that IL34 is a Treg-specific cytokine that may play a crucial role in Treg-mediated tolerance. More precisely, we observed that about half of the Foxp3$^+$ Tregs (CD4$^+$ or CD8$^+$) express IL34 (FIG. 1C).

As we suspected a strong suppressive potential of IL34 in human, we added different doses of soluble human IL34 to a MLR where CD4$^+$CD25$^−$CFSE-labelled effector T cells were in presence of T-depleted allogeneic APCs. We observed a significant inhibition of effector T cells proliferation in presence of 5 µg/ml of IL34, thus confirming the dose-dependent suppressive potential of IL34 on anti-donor immune response.

Altogether, these data provided the proof of concept of IL34 as a Treg-specific protein and a potential therapeutic target in manipulating the anti-donor immune response.

Discussion:

The biological relevance of IL34 remains to date largely unknown and controversial. In our study, in an attempt to unravel the complex mechanisms of tolerance induction in transplantation, we provide evidences, for the first time, of the unexpected properties of IL34 as a master regulator of immune responses and tolerance. We also provide the first proof that IL34 can be expressed by CD8$^+$CD45RC$^{low}$ Tregs, and most importantly can induce potent regulatory T cells.

We analyzed IL34 expression by human Foxp3$^+$ CD45RC$^{low}$ CD4$^+$ and CD8$^+$ Tregs. Strikingly, we observed a specific and unique high level expression of IL34 by Foxp3$^+$CD45RC$^{low}$ CD4$^+$ and CD8$^+$ Tregs, while CD45RC$^{high}$ and Foxp3$^−$CD45RC$^{low}$ CD4$^+$ and CD8$^+$ T cells did not, demonstrating that IL34 is a Treg-specific cytokine in human. In addition, we also demonstrated the ex vivo suppressive potential of IL34 by itself on the anti-donor immune response, suggesting its potential as a target therapeutic in transplantation, and by extension in autoimmune diseases.

In conclusion, we described here the role in transplantation tolerance of a new cytokine, IL34, and we revealed its potential as a therapy in transplantation and by extension in other diseases. We also demonstrated for the first time that this cytokine can be produced by Tregs, opening new possibilities in the generation of Tregs transferrable to the human setting.

REFERENCES

Throughout this application, various references describe the state of the art to which this invention pertains. The disclosures of these references are hereby incorporated by reference into the present disclosure.
1. Waldmann, H., Hilbrands, R., Howie, D., and Cobbold, S. 2014. Harnessing FOXP3+ regulatory T cells for transplantation tolerance. *J Clin Invest* 124:1439-1445.
2. Robb, R. J., Lineburg, K. E., Kuns, R. D., Wilson, Y. A., Raffelt, N. C., Olver, S. D., Varelias, A., Alexander, K. A., Teal, B. E., Sparwasser, T., et al. 2012. Identification and expansion of highly suppressive CD8(+)FoxP3(+) regulatory T cells after experimental allogeneic bone marrow transplantation. *Blood* 119:5898-5908.
3. Wei, S., Nandi, S., Chitu, V., Yeung, Y. G., Yu, W., Huang, M., Williams, L. T., Lin, H., and Stanley, E. R. 2010. Functional overlap but differential expression of CSF-1 and IL-34 in their CSF-1 receptor-mediated regulation of myeloid cells. *J Leukoc Biol* 88:495-505.
4. Ordonez, L., Bernard, I., L'Faqihi-Olive, F. E., Tervaert, J. W., Damoiseaux, J., and Saoudi, A. 2009. CD45RC isoform expression identifies functionally distinct T cell subsets differentially distributed between healthy individuals and AAV patients. *PLoS One* 4:e5287.

5. Ordonez, L., Bernard, I., Chabod, M., Augusto, J. F., Lauwers-Cances, V., Cristini, C., Cuturi, M. C., Subra, J. F., and Saoudi, A. 2013. A higher risk of acute rejection of human kidney allografts can be predicted from the level of CD45RC expressed by the recipients' CD8 T cells. *PLoS One* 8:e69791.

The invention claimed is:

1. A method for labeling, detecting and/or isolating forkhead box P3 (Foxp3+) regulatory T cells (Foxp3+ Treg cells) from a biological sample containing peripheral blood mononuclear cells (PBMC) or lymphocytes comprising the following steps of:
   (i) coupling the surface of PBMC or lymphocytes to a capture moiety which binds to the cell through a cell surface molecule and to Interleukin-34 (IL34),
   (ii) culturing the lymphocytes under conditions wherein IL34 is secreted, released and specifically captured by the capture moiety, (iii) labeling the IL34 expressing lymphocytes with a label moiety, and
   (iv) optionally, detecting and/or isolating said IL34 expressing lymphocytes which are Foxp3+ Treg cells, wherein the cell surface molecule is selected from the group consisting of CD3, CD4, CD8, CD45, TCR, IFNγ, and IL10.

2. The method according to claim 1, wherein the capture moiety is selected from the group consisting of a bispecific antibody which binds to CD3 and IL34, a bispecific antibody which binds to CD4 and IL34, a bispecific antibody which binds to CD8 and IL34, a bispecific antibody which binds to CD45 and IL34, and a bispecific antibody which binds to a TCR and IL34.

3. The method according to claim 1, wherein the capture moiety is selected from the group consisting of a trispecific antibody which binds to IL34, IFNγ and CD3, a trispecific antibody which binds to IL34, IL10 and CD3, a trispecific antibody which binds to IL34, and a trispecific antibody which binds to IL34, CD3 and a cell surface molecule selected from the group consisting of CD4, CD8, CD45, and TCR.

4. The method according to claim 1, wherein the label moiety is a labeled anti-IL34 antibody.

5. The method according to claim 1, wherein the biological sample is a blood sample obtained from a transplanted patient or a patient suffering from an autoimmune disease, allergy or cancer.

6. The method according to claim 1, wherein said method is for obtaining a population of antigen-specific Foxp3+ Treg cells, and wherein said method comprises a step of culturing the population of Foxp3+ Treg cells with a culture medium comprising an amount of antigen and a step of isolating the population of antigen-specific Foxp3+ Treg cells.

7. The method according to claim 1, wherein said method is an in vitro method for determining whether a patient is at risk of transplant rejection, autoimmune diseases, unwanted immune response against therapeutic proteins or allergies, wherein said method comprises a step of determining the presence Foxp3+ Treg cells in a biological sample obtained from said patient, and wherein the presence of Foxp3+ Treg cells is indicative of a reduced risk of transplant rejection, autoimmune diseases, unwanted immune response against therapeutic proteins or allergies.

8. The method according to claim 1, wherein said method is an in vitro method for predicting the survival time of a subject suffering from a cancer, wherein said method comprises the steps of determining the presence Foxp3+ Treg cells in a biological sample obtained from said subject, and concluding that the presence of Foxp3+ Treg cells is indicative of a poor prognosis.

9. A kit comprising at least one capture moiety which binds to the cell through a cell surface molecule and to IL34, wherein the cell surface molecule is selected from the group consisting of CD3, CD4, CD8, CD45, TCR, IFNγ and IL10.

10. The kit according to claim 9, further comprising a labeled moiety.

11. The kit according to claim 9, wherein the at least one capture moiety which binds to the cell through a cell surface molecule and to IL34 is selected from the group consisting of a bispecific antibody which binds to CD3 and IL34, a bispecific antibody which binds to CD4 and IL34, a bispecific antibody which binds to CD8 and IL34, a bispecific antibody which binds to CD45 and IL34, and a bispecific antibody which binds to a TCR and IL34.

12. The kit according to claim 10, wherein the label moiety is a labeled anti-IL34 antibody.

13. The kit according to claim 9, wherein the at least one capture moiety which binds to the cell through a cell surface molecule and to IL34 is selected from the group consisting of a trispecific antibody selected from the group consisting of a trispecific antibody which binds to IL34, IFNγ and CD3, a trispecific antibody which binds to IL34, IL10 and CD3 and a trispecific antibody which binds to IL34, CD3 and a cell surface molecule selected from the group consisting of CD4, CD8, CD45, and TCR.

14. An isolated population of Foxp3+ Treg cells obtainable by a method according to claim 1, wherein said Foxp3+ Treg cells comprise both CD4+ Foxp3+ Treg cells and CD8+ Foxp3+ Treg cells.

15. The isolated population of Foxp3+ Treg cells according to claim 14, wherein said Foxp3+ Treg cells are antigen-specific Foxp3+ Treg cells.

16. A method for inducing immune tolerance and/or for suppressing and/or inhibiting immune responses in a subject, comprising administering to the subject an isolated population of Foxp3+ cells according to claim 14.

17. The method according to claim 16, for treating an autoimmune disease, graft rejection, any unwanted immune reaction against a therapeutic protein, or allergy.

* * * * *